(12) United States Patent
Nair et al.

(10) Patent No.: US 10,940,109 B2
(45) Date of Patent: Mar. 9, 2021

(54) MULTILAYER POLYMERIC MATRIX BASED MEDICAL DEVICES

(71) Applicant: The Regents of the University of Colorado, Denver, CO (US)

(72) Inventors: Devatha P. Nair, Denver, CO (US); Eric Dailing, Nashville, TN (US); Jeffrey W. Stansbury, Centennial, CO (US); Malik Y. Kahook, Aurora, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 15/507,219

(22) PCT Filed: Aug. 27, 2015

(86) PCT No.: PCT/US2015/047131
§ 371 (c)(1),
(2) Date: Feb. 27, 2017

(87) PCT Pub. No.: WO2016/033295
PCT Pub. Date: Mar. 3, 2016

(65) Prior Publication Data
US 2017/0239176 A1 Aug. 24, 2017

Related U.S. Application Data

(60) Provisional application No. 62/042,754, filed on Aug. 27, 2014.

(51) Int. Cl.
*A61K 9/00* (2006.01)
*B29D 11/00* (2006.01)
(Continued)

(52) U.S. Cl.
CPC .............. *A61K 9/0051* (2013.01); *A61F 2/16* (2013.01); *A61K 31/573* (2013.01); *A61K 47/32* (2013.01);
(Continued)

(58) Field of Classification Search
None
See application file for complete search history.

(56) References Cited

U.S. PATENT DOCUMENTS

| 4,727,011 A | 2/1988 | Mahabadi et al. |
| 5,529,914 A * | 6/1996 | Hubbell ............... A61K 9/1635 435/182 |

(Continued)

FOREIGN PATENT DOCUMENTS

WO  2013142354 A1  9/2013

OTHER PUBLICATIONS

WIPO, International Search Report, dated Jan. 6, 2016.
(Continued)

*Primary Examiner* — Dominic Lazaro
(74) *Attorney, Agent, or Firm* — Cantor Colburn LLP (57) ABSTRACT

The disclosure relates to multilayer polymeric matrix based medical devices. In one example, a device comprises an inner first polymeric matrix and an outer second polymeric matrix. The addition of second polymeric matrix modifies bulk properties of each matrix thus resulting in a device where specific bulk properties are incorporated. The disclosure also relates to methods of manufacturing various embodiments of medical devices and their uses.

21 Claims, 9 Drawing Sheets

(51) Int. Cl.
  *G02B 1/04*   (2006.01)
  *A61F 2/16*   (2006.01)
  *A61K 47/32*  (2006.01)
  *A61K 31/573* (2006.01)
  *A61L 27/50*  (2006.01)
  *A61L 27/58*  (2006.01)
  *G02C 7/04*   (2006.01)
  *A61L 27/54*  (2006.01)
  *A61L 27/34*  (2006.01)
  *A61L 27/14*  (2006.01)

(52) U.S. Cl.
  CPC .............. *A61L 27/14* (2013.01); *A61L 27/34* (2013.01); *A61L 27/50* (2013.01); *A61L 27/54* (2013.01); *A61L 27/58* (2013.01); *B29D 11/00038* (2013.01); *B29D 11/0075* (2013.01); *G02B 1/043* (2013.01); *G02C 7/04* (2013.01)

(56) References Cited

U.S. PATENT DOCUMENTS

| | | | |
|---|---|---|---|
| 5,834,274 A * | 11/1998 | Hubbell | A61L 26/0019 435/177 |
| 2009/0186093 A1 | 7/2009 | Liu et al. | |
| 2010/0272808 A1 | 10/2010 | Berner et al. | |
| 2012/0136322 A1 * | 5/2012 | Alster | A61F 9/0017 604/290 |
| 2014/0127309 A1 | 5/2014 | Drake et al. | |
| 2014/0200678 A1 | 7/2014 | Detamore et al. | |

OTHER PUBLICATIONS

Chen et al., "Tuning the surface microstructure and gradient properties of polymers with photopolymerizable polysiloxane-modified nanogels" RSC Adv. 2014, 4, 28928-28936.

Dailing, et al., "Photopolymerizable Nanogels as Macromolecular Precursors to Covalently Crosslinked Water-Based Networks" Soft Matter. Jul. 28, 2015, 11(28): 5647-5655 (doi:10.1039/c4srn02788d).

Moraes et al., "Control of polymerization shrinkage and stress in nanogel-modified monomer and composite materials" Dental Materials 27 (2011) 509-519.

Written Opinion dated Jan. 6, 2016; International Application No. PCT/US15/47131; International Filing Date Aug. 27, 2015 (6 pages).

* cited by examiner

MULTILAYER POLYMERIC MATRIX BASED MEDICAL DEVICES

BACKGROUND

Altering physical and mechanical properties of a medical device without compromising its core function is challenging. For example, in the ophthalmic field, discomfort due to dry eye syndrome for contact lens users ("CLDE") has been acknowledged as the primary reason for the discontinuing use of contact lenses ("CL"). The causes of CLDE are multi-faceted and contribute to the complexity of addressing the problem. One sustainable way to minimize the impact of dry eye or CLDE is to modify the CL to elute dry-eye drug(s). However, effective ways to deliver a drug on a CL are still challenging due to requirements of maintaining the core function of the CL, for example, modification of a corrective contact lens should not alter its core function of improving vision and optical clarity.

The present disclosure is directed toward overcoming one or more of the problems discussed above.

SUMMARY OF THE DISCLOSURE

In an embodiment, the disclosure provides a medical device comprising: an inner core of a first polymeric matrix having a first bulk property; an outer layer of a second polymeric matrix having a second bulk property; wherein the first polymeric matrix is covalently linked with the second polymeric matrix via an interfacial polymerization reaction forming a polymeric macroscopic cross-linked network; and further wherein the interfacial polymerization reaction modifies the first bulk property of the first polymeric matrix, and the second bulk property of the second polymeric matrix.

The first polymeric matrix of the device may be a cross-linked polymer or a linear polymer or a combination thereof such as polyurethane, poly(ethylene, glycol), poly(propylene glycol), polyvinyl alcohol, acrylic acid, methacrylic acid, chitosan, alginates, crylamides, epoxies, isocyanates vinyl ethers, allyl ethers, acrylates, methacrylates, acrylamides, nanogels, or nanoparticles, or nanotubes.

The second polymeric matrix of the device may be a cross-linked polymer or a linear polymer or a combination thereof such as hydrophilic or hydrophobic nanogels, nanotubes, poly(propylene glycol), polyvinyl alcohol, polyurethanes, isocyanates, polyvinyl alcohol, acrylic acid, methacrylic acid, chitosan, alginates, acrylamides, and nanoparticles, acrylates and methacrylates.

A medical device in accordance with embodiments herein may include one or more bulk properties. In some aspect, a CL, for example, may have a first bulk parameter associated with a first polymeric matrix and a second bulk parameter associated with a second polymeric matrix.

The first and the second bulk property may be independently of each other and can be a refractive index, a glass transition temperature, a tackiness, or the like.

The first and second polymeric matrix of the device are covalently linked via the interfacial polymerization reaction selected from the group consisting of redox reactions, photoinitiation reaction, thermal initiation reaction, Michael addition, polymer brushes reaction, and cationic initiator reaction.

In an embodiment, the first polymeric matrix of the device comprises at least one pharmaceutically active compound, and the second polymeric matrix is chemically modified to provide for a controlled release of the at least one pharmaceutically active compound.

In this regard, the first polymeric matrix of the device can comprise one or more pharmaceutically active compound from about 0.5 wt % to about 95 wt % of the first polymeric matrix.

The pharmaceutically active compound contained in the first polymeric matrix may be within or on the first polymeric matrix.

In typical embodiment, the first polymeric matrix is impregnated with at least one pharmaceutically active compound.

The second polymeric matrix of the device may be transparent.

In an embodiment, the second polymeric matrix of the device is chemically modified to alter a bulk property of the device, or a bulk property of just the second polymeric matrix. Further, the interfacial polymerization reaction between the first and second polymeric layers may alter the bulk property of the first polymeric layer as well.

In an embodiment, the second polymeric matrix of the device is chemically modified to alter a refractive index of the device, or the second polymeric matrix. Further, the interfacial polymerization reaction between the first and second polymeric layer may alter the refractive index of the first polymeric layer.

In an embodiment, the second polymeric matrix of the device is chemically modified to alter a glass transition temperature of the device, or the second polymeric matrix. Further, the interfacial polymerization reaction between the first and second polymeric layer may alter the glass transition temperature of the first polymeric layer.

The design of the medical devices may encompass the following non-limiting criteria:

1) In some instances when the medical device is used to control delivery of one or more pharmaceutically active compounds, the second outer layer is designed by using specific polymers that result in desired mesh size, polarity, and/or hyphobic/hydrophilic balance. Further, in some instances, when the medical device is a lens, the second polymeric matrix is designed to be transparent and/or modify refractive index of the resulting device. Exemplary second layer(s) are multiple cross-linked nanogel layers of different mesh sizes—such as different loadings of-EHEMA/IBMA based nanogels.

2) In other instances when the medical device is designed to reduce tackiness of the first polymeric matrix, then the second polymeric matrix is designed to incorporate polymers that can provide hydrophobic matrix. Exemplary second layer(s) are UDMA/IBMA based nanogels.

3) In instances when reduction of glistening of the first polymeric matrix is desired, then the second polymeric matrix is designed to alter the properties of the bulk composite polymer, for example, by altering the amount of water uptake of the network as a whole by the presence of the coating.

The device may be an ophthalmic device, for example, a contact lens, or refractive index correction device, drug delivery device, ophthalmic implantation device.

The device may be a pathology treatment device.

The pharmaceutically active compound contained in the first polymeric matrix may be an anti-glaucoma medications, carbonic anhydrase inhibitors, parasympathomimetics, prostaglandins and hypotensive lipids, antimicrobial agent, anti-inflammatory, an agent that prevents of modifies an allergic response, a mast cell stabilizer, cycloplegic, mydriatic or the like, thrombin inhibitors; antithrombogenic agents; thrombolytic agents; fibrinolytic agents; vasospasm inhibitors; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluorometholone, betamethasone, triamcinolone, triamcinolone acetonide); non-steroidal anti-inflammatories (NSAIDs) (such as salicylate, indomethacin, ibuprofen, diclofenac, flurbiprofen, piroxicam indomethacin, ibuprofen, naxopren, piroxicam and nabumetone). Examples of such anti-inflammatory steroids contemplated for use with the present lacrimal implants, include triamcinolone acetonide (generic name) and corticosteroids that include, for example, triamcinolone, dexamethasone, fluocinolone, cortisone, prednisolone, flumetholone, and derivatives thereof); antiallergenics (such as sodium chromoglycate, antazoline, methapyriline, chlorpheniramine, cetrizine, pyrilamine, prophenpyridamine); anti proliferative agents (such as 1,3-cis retinoic acid, 5-fhiorouracil, taxol, rapamycin, mitomycin C and cisplatin); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil; immunological drugs (such as vaccines and immune stimulants); hormonal agents (such as estrogens, estradiol, progestational, progesterone, insulin, calcitonin, parathyroid hormone, peptide and vasopres sin hypothalamus releasing factor); immunosuppressive agents, growth hormone antagonists, growth factors (such as epidermal growth factor, fibroblast growth factor, platelet derived growth factor, transforming growth factor beta, somatotrapin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix; components; ACE inhibitors; free radical scavengers; chelators; antioxidants; anti polymerases; photodynamic therapy agents; gene therapy agents; and other therapeutic agents such as prostaglandins, antiprostaglandins, prostaglandin precursors, including antiglaucoma drugs including beta-blockers such as Timolol, betaxolol, levobunolol, atenolol, and prostaglandin analogues such as bimatoprost, travoprost, latanoprost etc.; carbonic anhydrase inhibitors such as acetazolamide, dorzolamide, brinzolamide, methazolamide, dichlorphenamide, diamox; and neuroprotectants such as lubezole, nimodipine and related compounds; and parasympathomimetrics such as pilocarpine, carbachol, physostigmine and the like.

The device may also define a securement portion such as a through hole or an aperture for securing the device to a site of implantation in the body of a subject. For example, the securement portion may provide one or more apertures for securing the device to a site within or on the subject by suturing. A subject herein refers to a mammal and more typically a primate or human.

In an embodiment the device is a CL and may be inserted on or in at least one eye of a subject, in or on periocular tissues of the tear drainage system or lids of a subject, in the orbital compartment of the eye of a subject, or in the anterior or posterior portions of the eye of a subject.

The device may also be inserted in or on parts of a mammal proximate to the area of disease for which the device is targeting.

The second polymeric matrix of the device may degrade by hydration, ultraviolet or visible light exposure, or temperature change.

The device may be biodegradable.

In an embodiment, the inner polymeric matrix of the device may have a tack quotient from about 0.5 to about 3.0, from about 1.0 to about 2.0, or from about 1 to 1.50.

The second polymeric matrix of the device may degrade after implantation by hydration, ultraviolet or visible light exposure, or temperature change.

The second polymeric matrix of the device has a microvacuole value equal to or less than about 40 MVs/mm$^2$.

The first polymeric matrix of the device may degrade by hydration, ultraviolet or visible light exposure, or temperature change releasing at least one pharmaceutically active compound, without any change in the shape and/or form of the device and/or the second polymeric matrix.

The second polymeric matrix degrades by hydration, ultraviolet or visible light exposure, or temperature change releasing at least one pharmaceutically active compound from the first polymeric matrix, without any change in the shape and/or form of the device and/or the first polymeric matrix.

The inner first polymeric matrix of the device may be capable of undergoing a second redox reaction with the outer second polymeric matrix forming a nanotube.

In another embodiment, the disclosure provides a method of manufacturing a medical device as described above, the method comprising the steps of: forming an inner core comprising a first polymeric matrix having a first bulk property from a cross-linking polymer or a linear polymer or a combination thereof; optionally swelling the first polymeric matrix with at least one pharmaceutically active compound; forming an outer layer of a second polymeric matrix having a second bulk property from a cross-linking polymer or a linear polymer or a combination thereof; covalently linking the first polymeric matrix and the second polymeric matrix via an interfacial polymerization reaction forming a polymeric macroscopic cross-linked network, further wherein the interfacial polymerization reaction modifies the first bulk property of the first polymeric matrix, and the second bulk property of the second polymeric matrix; isolating the polymeric macroscopic cross-linked network to form a solid medical device; optionally creating a securing portion in the device; and optionally covalently linking the first polymeric matrix and the second polymeric matrix via a second interfacial polymerization reaction forming a nanotube.

The interfacial polymerization reaction of the method may be a redox reaction, photoinitiation reaction, thermal initiation reaction, Michael addition, polymer brushes reaction, or cationic initiator reaction.

In another embodiment, the disclosure provides a method of treating a mammal with glaucoma, infection, allergy, inflammation, pain, dry eye disease, refractive deficit or other ocular or systemic diseases treated with a pharmaceutically active compound with the device, the method comprising inserting the device containing the pharmaceutically active compound in or on the mammal. The mammal may be a human or an animal.

In another embodiment, the disclosure provides a method of manufacturing a medical device, the method comprising the steps of: forming an inner core comprising a first polymeric matrix having a first bulk property from a cross-linking polymer or a linear polymer or a combination thereof; optionally swelling the first polymeric matrix with at least one pharmaceutically active compound; forming a second polymeric matrix having a second bulk property from a cross-linking polymer or a linear polymer or a combination thereof; covalently linking the first polymeric matrix and the second polymeric matrix via an interfacial polymerization reaction forming a polymeric macroscopic cross-linked network in a mold, further wherein the interfacial polymerization reaction modifies the first bulk property of the first polymeric matrix, and the second bulk property of the second polymeric matrix; preventing the polymeric macroscopic cross-linked network formed in the mold from shrinking via a covalent bond, hydrophobic interaction, hydrophilic interaction, van der Waals interaction or hydrogen bond between the mold and the second outer polymeric matrix; isolating the polymeric macroscopic cross-linked network to form a solid medical device; optionally creating securing portion in the device; and optionally covalently linking the first polymeric matrix and the second polymeric matrix via a second interfacial polymerization reaction forming a nanotube.

The mold used to manufacture the device may comprise in or on the surface of the mold, for example, sulfhydryl groups or reactive carbon comprising functional groups to form a disulfide linkage or a carbon-carbon linkage resulting in covalent bonds with the second polymeric matrix, alginate groups for hydrophilic interactions with the second polymeric matrix, polyethylene groups for van der Waals interaction with the second polymeric matrix, polyurethane groups for hydrogen bond formation with the second polymeric matrix, vinyl sulfone groups for polar bond with the second polymeric matrix.

In an embodiment, the mold used to manufacture the device is the second polymeric matrix. The resulting device comprises a first polymeric matrix but lacks the second polymeric matrix. In this regard, the second layer of polymeric matrix is constructed as a mold and to this mold is added the first polymeric matrix to manufacture a solid medical device. This design permits to construct a device where the second polymeric matrix acting as a mold prevents shrinking of the first polymeric matrix upon solidification by forming covalent bonds or other interactions with the first polymeric matrix via interfacial polymerization reaction.

In an embodiment, the disclosure provides a method of manufacturing a medical device, the method comprising the steps of: forming a mold from a second polymeric matrix using a cross-linking polymer or a linear polymer or a combination thereof; forming an inner core comprising a first polymeric matrix having a first bulk property from a cross-linking polymer or a linear polymer or a combination thereof; optionally swelling the first polymeric matrix with at least one pharmaceutically active compound; adding the first polymeric matrix to the mold to form a solid medical device comprising the first polymeric matrix; preventing the solid medical device in the mold from shrinking via a covalent bond, hydrophobic interaction, hydrophilic interaction, van der Waals interaction or hydrogen bond between the mold and the first polymeric matrix; isolating the solid medical device from the mold; and optionally creating securing portion in the device.

The first polymeric matrix used to manufacture the device using a mold comprising the second polymeric matrix can be synthesized from a cross-linked polymer or a linear polymer or a combination thereof, for example, polyurethane, poly (ethylene glycol), poly(propylene glycol), polyvinyl alcohol, acrylic acid, methacrylic acid, chitosan, alginates, acrylamides, epoxies, isocyanates vinyl ethers, allyl ethers, acrylates, methacrylates, acrylamides, nanogels, or nanoparticles, nanotubes.

The mold may be manufactured from a second polymeric matrix. The second polymeric matrix can be a cross-linked polymer or a linear polymer or a combination thereof. For example, hydrophilic or hydrophobic nanogels, nanotubes, poly(propylene glycol), polyvinyl alcohol, polyurethanes, isocyanates, polyvinyl alcohol, acrylic acid, methacrylic acid, chitosan, alginates, acrylamides, and nanoparticles, acrylates and methacrylates.

The covalent bond formation between the mold and the first polymeric matrix is effected by a chemical reaction. For example, redox reactions, photoinitiation reaction, thermal initiation reaction, Michael addition, polymer brushes reaction, and cationic initiator reaction.

Other embodiments of the disclosure are described herein. The features, utilities and advantages of various embodiments of this disclosure will be apparent from the following more particular description of embodiments as illustrated in the accompanying drawings.

BRIEF DESCRIPTION OF THE DRAWINGS

These and other features and advantages of the present disclosure will be better understood by reference to the following detailed description when considered in conjunction with the accompanying drawing wherein:

FIGS. 1(a), 1(b), 1(c), 1(d), 1(e), and 1(f) show illustrative monomers utilized in the synthesis of dimethacrylate hydrophilic and hydrophobic nanogels. In FIG. 1(f), m and n are each independently an integer, e.g., 0, 1, 2, 3, 4, 5, 10, 20, 30, 40, 50, or 100.

FIG. 3 shows schematic representation of the synthesis route of a hydrophilic nanogels. Gel Permeation Chromatography (GPC) was utilized to characterize the molecular weight of the nanogels and the hydrodynamic Rh, which is defined as the mass weighted average distance from the core of a molecule to each mass element in the molecule

DETAILED DESCRIPTION

General terms used in any of the embodiments herein can be defined as follows, however, the meaning stated should not be interpreted as limiting the scope of the term per se. Unless defined otherwise, all technical and scientific terms used herein have the same meaning as commonly understood by one of ordinary skill in the art to which this invention belongs.

The words "comprise", "comprising", "include" and "including" when used in this specification and in the following claims are intended to specify the presence of the stated features, components, or steps, but they do not preclude the presence or addition of one or more additional features, components, or steps thereof.

Nanogels, as used herein are described as polymeric nanoparticles of a fixed, characteristic internal network structure with dimensions below 100 nm and with an inbuilt ability to react further and form cross-linked networks.

Hydrogel or hydrophilic nanogel as used herein are a network of hydrophilic polymeric chains. For example HEMA, TEGDMA and PEG based nanogels.

Hydrophobic nanogel as used herein is a network of hydrophobic polymeric chains. For example Spiropyran, Urethane, Epoxy, Isocyanate-based nanogels.

Nanotubes as used herein refer to a material with two dimensions in the nanometer scale that are either incorporated with a polymer or are self-assembling structures that form as result of the polymerization reaction. For example, self-assembling structures that form within the first or the second polymeric matrix.

Redox reactions as used herein refer to a reaction where oxidation states of some components involved in the reaction changes. For example using TEMED/APS (or Riboflavin), Fentons reagent.

Photoinitiation reaction as under herein refer to a reaction where a photoinitiator introduced in the reaction produces polymerizing radicals when exposed to light. For example incorporating the photoinitiator (IR819, IR651, I2959) into a hydrogel.

Thermal initiation reaction as used herein refers to a reaction where a thermal initiator initiates polymerization upon heating. For example incorporating the thermal initiator (AIBN, Lauryl Peroxide) into a hydrogel.

Michael addition as used herein refer to a 1,4-addition reaction of α-β-unsaturated carbonyl compounds or α-β-unsaturated nitriles such as a nucleophilic addition of a carbanion or another nucleophile to an α-β-unsaturated carbonyl. Exemplary nucleophile or a base catalyst are triethylamine, triphenylphosphene to initiate the reaction.

Polymer brushes reaction as used herein refer to polymeric brushes in which a polymeric assembly is tethered via a reaction on the coating either through covalent attachment and/or a physical entanglement. For example using linear polymer brushes attached to solid substrate surfaces using the cationic reaction.

Cationic initiator reaction as used herein refer to chain growth polymerization where cationic initiator initiates the chain growth by transferring charge to a monomer making the monomer reactive for chain growth. Exemplary cationic initiator are photobased and acid based catalyst such as Borontrifluoride and the like.

Bulk property as used herein refer to specific molecular weights, polydispersity, branching density, internal free volume, glass transition temperature ($T_g$), hydrophilic/hydrophobic balance, mesh sizes on the surface of the core material, glistening, tackiness, refractive index, optical properties, magnetic properties, elastic modulus, hydrolytic stability, viscoelastic properties.

The "wt %" or "weight percent" is based on the total weight of the polymeric matrix. For example, 5 wt % of the active pharmaceutical compound in the first polymeric matrix means that the active pharmaceutical compound added to the first polymeric matrix is 90 wt % of the total weight of the first polymeric matrix.

"Tack Quotient" as used herein is used to quantify the tackiness of the medical device, such as an intraocular lens, and it is determined by measuring the maximum load required to separate two pieces of the same material. This measure is then compared to that of a 'standard' material and defines the ratio of the tack of the test material to that of the standard material is defined as the "Tack Quotient." For example, intraocular lens materials having a Tack Quotient higher than about 3 in this test generally present handling problems that may make them unsuitable for use as a foldable intraocular lens material.

Glistening as used herein is evaluated based on the size and density of the microvacuole observed. Once the second polymeric matrix is implemented, the presence of microvacuoles within the medical device, such as a lens, is used to assess the lens. In an accelerated glistening test, each lens is placed in a constant temperature water bath set at 50°

C.±1° C. for 24 hours and subsequently moved to a 37° C.±1° C. water bath for 2 hours. The number of microvacuoles per square millimeter (MVs/mm$^2$) as determined via imaging is used to evaluate the glistening observed in the lens.

The disclosure provides various embodiments of a multilayer medical device for temporary or permanent implantation in a mammal for specific medical treatment. In one embodiment, the device contains two layers of polymeric matrices having different bulk properties and are covalently linked with each other to form a polymeric macroscopic cross-linked network via covalent bond formation. The covalent bond formation takes place via an interfacial polymerization reaction from reactive nanoscale (<50 nm) prepolymeric particles, which upon polymerization, form polymeric macroscopic cross-linked networks. The first layer is the inner first polymeric matrix that forms the core of the device. The second layer is the outer layer of the device and it comprises a second polymeric matrix. The bulk property of two layers may be altered as they undergo the interfacial polymerization reaction to form polymeric macroscopic cross-linked networks.

In an embodiment, the reactive nanoscale prepolymeric particles are present on at least one of the first polymeric matrix or the second polymeric matrix.

In an embodiment, the reactive nanoscale particles are present on the second polymeric matrix.

In another embodiment, the reactive nanoscale prepolymeric particles on the first polymeric matrix and the second polymeric matrix are different.

Non limiting examples of reactive nanoscale prepolymeric particles may include Graphite, or Phyllosilicates.

In an embodiment, the device comprises at least one pharmaceutically active compound. The outer layer is configured based on physical properties of the pharmaceutically active compound for purposes of controlled delivery. In another embodiment, the device is configured to modify the bulk properties of the inner and/or outer layers. For example, in the context of a contact lens, the contact lens containing pharmaceutically active compound is configured to act as the inner layer and it is then coated with a suitable second layer that is transparent to preserve optical clarity. The second layer is configured to control delivery of pharmaceutically active compound.

The design of the medical devices may encompass the following non-limiting criteria:
1) In some instances when the medical device is used to control delivery of pharmaceutically active compound, second outer layer is designed by using specific polymers that result in desired mesh size, polarity, and/or hyphobic/hydrophilic balance. Further, in some instances, when the medical device is a lens, the second polymeric matrix is designed to be transparent and/or modify refractive index of the resulting device. Exemplary second layer(s) are multiple cross-linked nanogel layers of different mesh sizes-such as different loadings of-EHEMA/IBMA based nanogels.
2) In other instances when the medical device is designed to reduce tackiness of the first polymeric matrix, then the second polymeric matrix is designed to incorporate polymers that can provide hydrophobic matrix. Exemplary second layer(s) are UDMA/IBMA based nanogels.
3) In instances when reduction of glistening of the first polymeric matrix is desired, then the second polymeric matrix is designed to alter the properties of the bulk composite polymer, for example, by altering the amount of water uptake of the network as a whole by the presence of the coating.

Embodiments disclosed herein are illustrated in greater detail by means of the non-limiting examples described herein.

EXAMPLES

The following examples are provided for illustrative purposes only and are not intended to limit the scope of the disclosure.

Materials

Figure 1A:
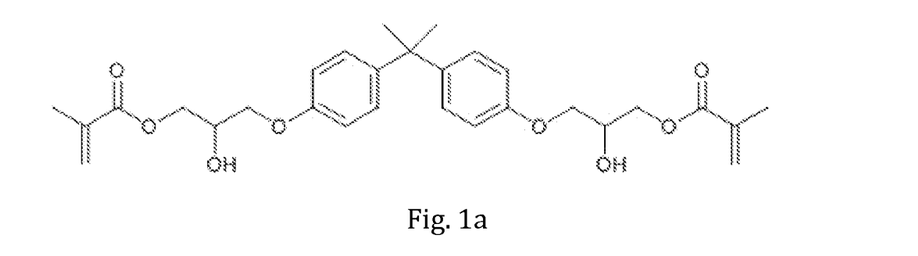
Figure 1B:
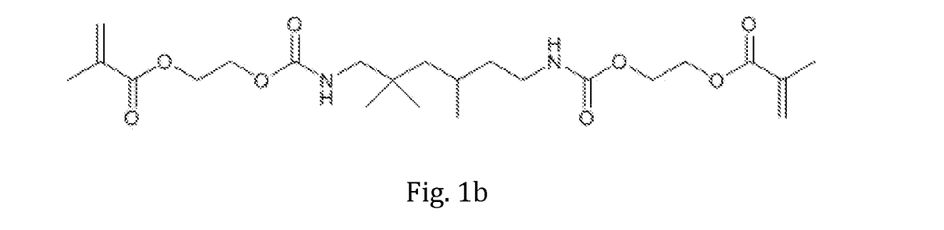
Figure 1C:
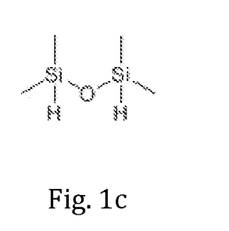
Figure 1D:
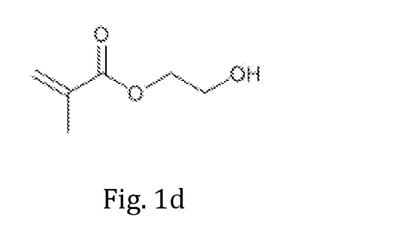
Figure 1E:
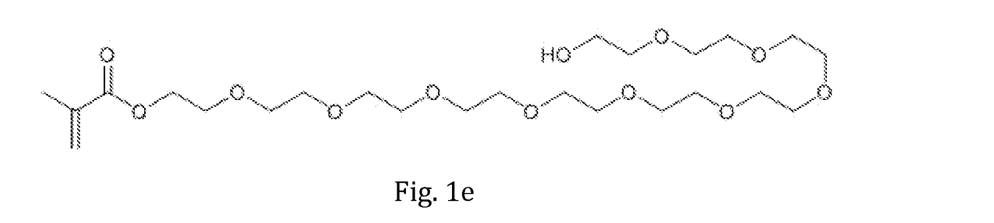
Figure 1F:
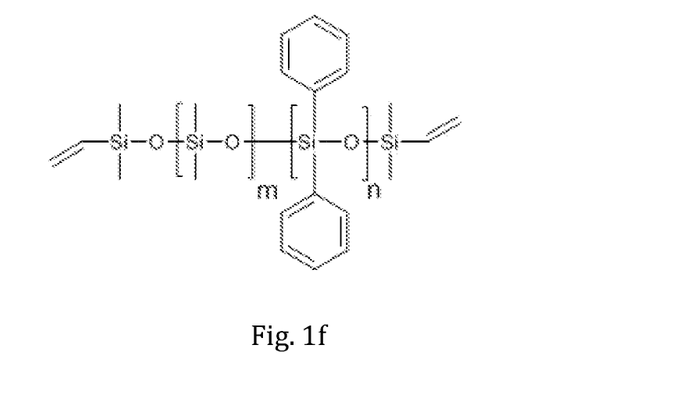

Polyethylene glycol methacrylate (EHEMA10, $M_n$=526) (FIG. 1(e)), tetraethylene glycol dimethacrylate (TTEGDMA), polyethylene glycol dimethacrylate (PEG550DMA, $M_n$=550), mercaptoethanol (ME), dibutyltin dilaurate, fluorescein acrylate, ammonium persulfate (APS) and azobisbutyronitrile (AIBN) were received from Sigma-Aldrich. Methanol and methyl ethyl ketone (MEK) were received from Fisher Scientific. Tetraethylmethylenediamine (TEMED) was received from TCI America. Isocyanatoethyl acrylate was received from Showa Denko. Polyfluor 570 (methacryloxyethyl thiocarbamoyl rhodamine B) was received from Polysciences. Dialysis membranes were received from SpectraPor. All materials were used as received except AIBN, which was recrystallized from methanol. FIGS. 1(a)-1(f) show illustrative monomers utilized in the synthesis of dimethacrylate hydrophilic and hydrophobic nanogels.

Example 1

Nanogel Preparation

Figure 2:
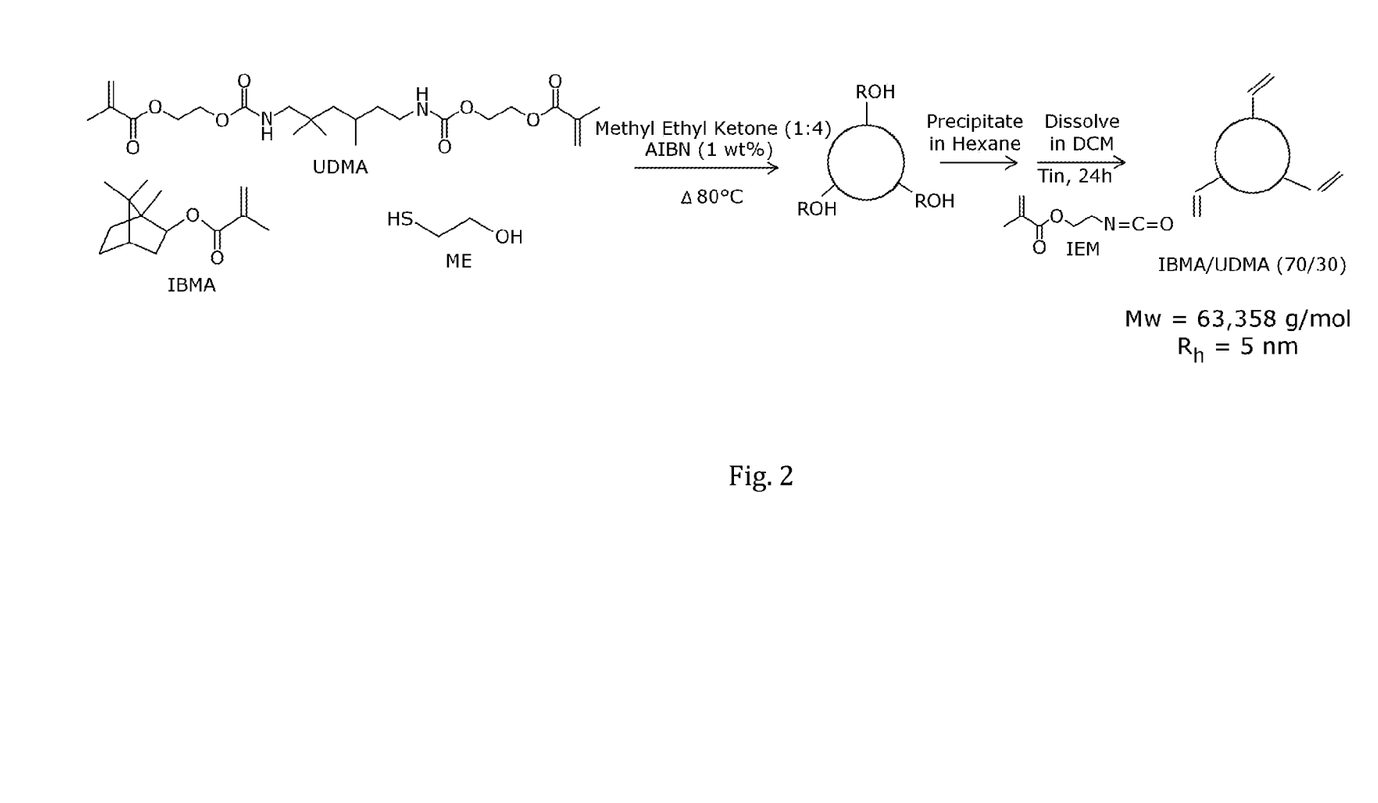
FIG. 2 shows schematic representation of the synthesis route of hydrophobic nanogels. Gel Permeation Chromatography (GPC) was utilized to characterize the molecular weight of the nanogels and the hydrodynamic of the nanogels.
Figure 3:
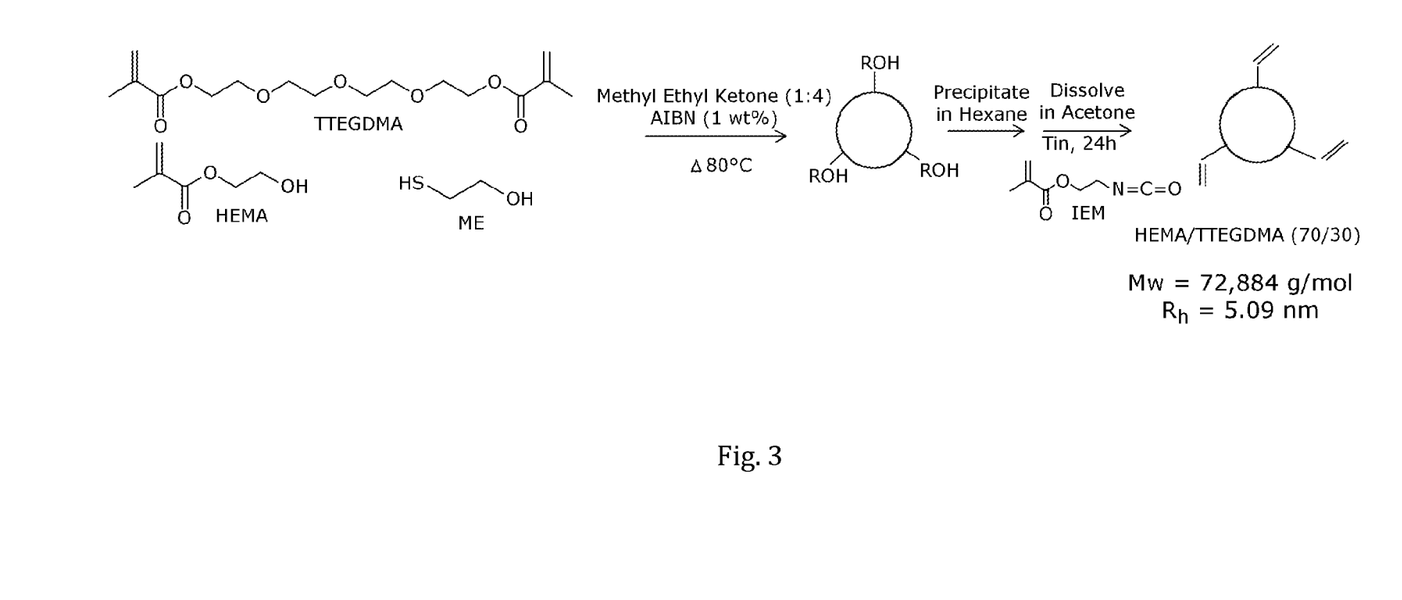

A 7:3 molar ratio of EHEMA10 to TTEGDMA or EHEMA5 to BisEMA was combined with 15 mol % ME, 0.1 wt % Polyfluor 570 and 1.0 wt % AIBN (relative to total monomer content) in a 6× volumetric excess of MEK. The reaction was purged with $N_2$ for 30 min and stirred at 75° C. for 6 hours, after which 90% conversion was achieved. 15 mol % IEA was added to the nanogel solution with approximately 10 mg dibutyltin dilaurate and stirred at room temperature for 24 hr. The nanogel solutions were concentrated, dialyzed in an 8000 MWCO membrane in methanol for 3 days and dried under reduced pressure. The development of the nanogels can start with the design of appropriate monomers from which the nanogels may be constructed followed by the use of these nanogels as the building blocks for the final polymer meshwork. The symmetric hydrophobic and hydrophilic dimethacrylate monomers and the nanogels formed therefrom are shown in FIG. 2 and FIG. 3 respectively.

Example 2

Hydrogel Preparation (Inner Core)

A solution of PEG550DMA with 1.0 wt % I2959 and 0.1 wt % fluorescein acrylate was loaded into silicon molds (5 mm×0.5 mm) and polymerized between glass slides for 5 minutes at 10 mW/cm2. A solution of 50 wt % nanogel in DI H2O with 1.0 wt % I2959 relative to nanogel mass was also prepared and polymerized for 10 minutes in the same conditions as the PEG550DMA gels. Following polymerization, all gels were stored in a solution of TEMED in DI $H_2O$ at the indicated concentrations for at least 24 hr. The API can be either swollen into the hydrogel or incorporated during the formation of the cross-linked network.

Example 3

Coating Procedure (Outer Second Layer)

Figure 4A:
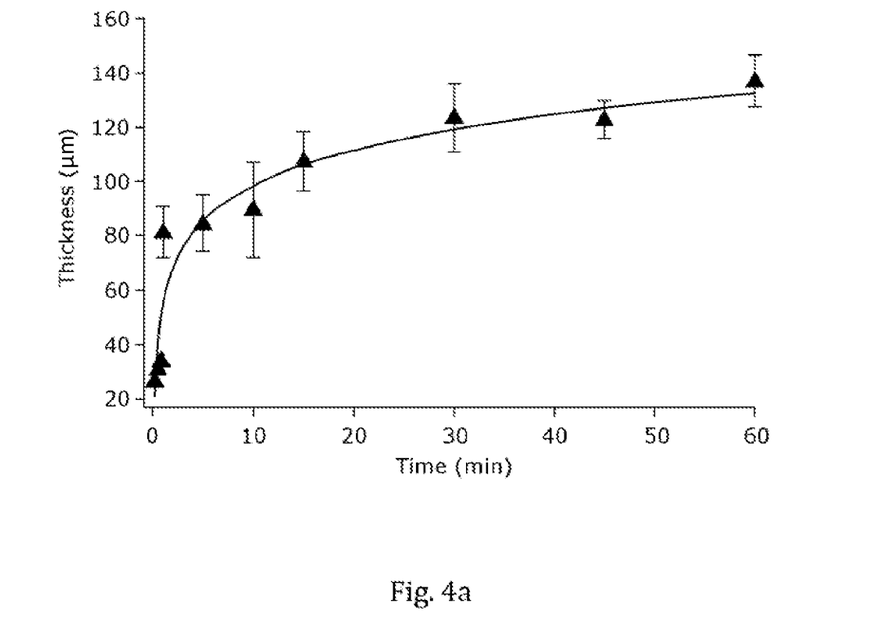
FIGS. 4(a), 4(b) show the growth of the nanogel coating layer on the surface of the core hydrogel as a function of time and is captured in FIG. 4(a). A PEG550DMA hydrogel with TEMED was placed in a solution of 25 wt % EHEMA10-TEGDMA nanogel in DI H2O with APS. A nanogel-APS solution of approximately 200 µL, was pipetted into each vial and the reaction was allowed to proceed for various amounts of time. Gels were then removed from the solution and stored in fresh DI H2O for at least 24 hr. The coating developed in the first one minute of exposure to the nanogel-immersing solution is captured in FIG. 4(b). Coating thickness was measured using ImageJ.
Figure 4B:
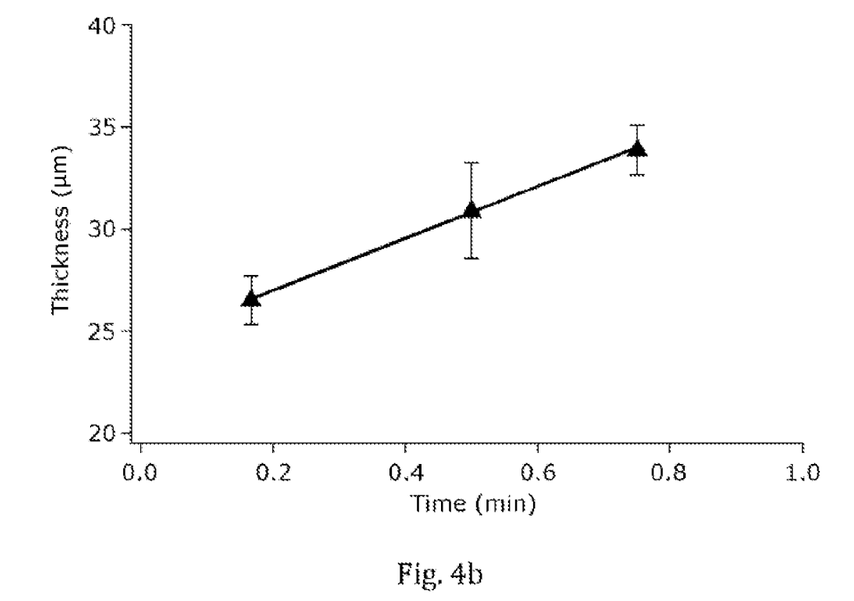

The coating material can be either a monomer, or polymer such as nanogel. A solution of 25 wt % EHEMA10-TTEGDMA nanogel was prepared in DI $H_2O$ with the indicated concentrations of APS. All solutions were freshly prepared prior to coating formation. Small sections of silicon rubber were glued to the bottom of a glass vial and a PEG550DMA or nanogel-based gel was placed on top to allow all gel surfaces to be in contact with the nanogel coating solution. A sufficient amount of nanogel-APS solution to cover the gel, approximately 200 μL, was pipetted into each vial and the reaction was allowed to proceed for various amounts of time. Gels were then removed from the solution and stored in fresh DI $H_2O$ for at least 24 hr. The growth of the nanogel coating layer on the surface of the core hydrogel as a function of time is captured in FIG. 4(a). The coating developed in the first one minute of exposure to nanogel-immersing solution is shown in FIG. 4b. Coating thickness was measured using ImageJ using a pixel-to-length calibration.

Confocal Microscopy

Figure 5A:
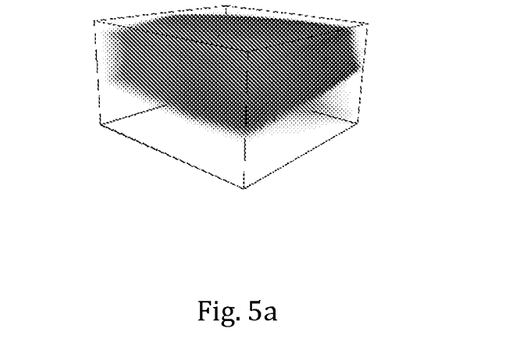
FIGS. 5(a), 5(b), 5(c) show Fluorescein-labeled core PEG hydrogel excited at 488 nm in the core material (FIG. 5(a)), the rhodamine-labeled nanogel coating at 561 nm is imaged to demonstrate the growth of a coating (FIG. 5(b)), and an overlay of the coating 510 and core 520 (FIG. 5(c)). Images were collected at 10× zoom and the three-dimensional Z stacks were collected at 10× zoom with a 10 μm step size.
Figure 5B:
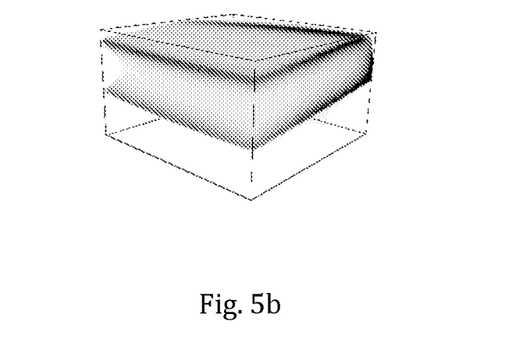
Figure 5C:
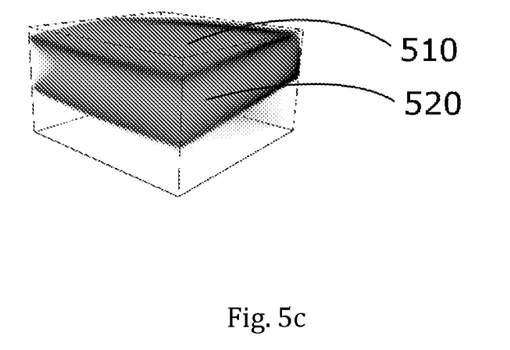

Images of the fluorescent hydrogel core and coating were obtained on a Nikon AIR confocal microscope (FIG. 5). Fluroescein was excited at 488 nm and rhodamine was excited at 561 nm and images were collected at 10× zoom. Three-dimensional Z stacks were collected at 10× zoom with a 10 μm step size.

Example 4

Controlled Release of a Pharmaceutically Active Compound.

Figure 6:
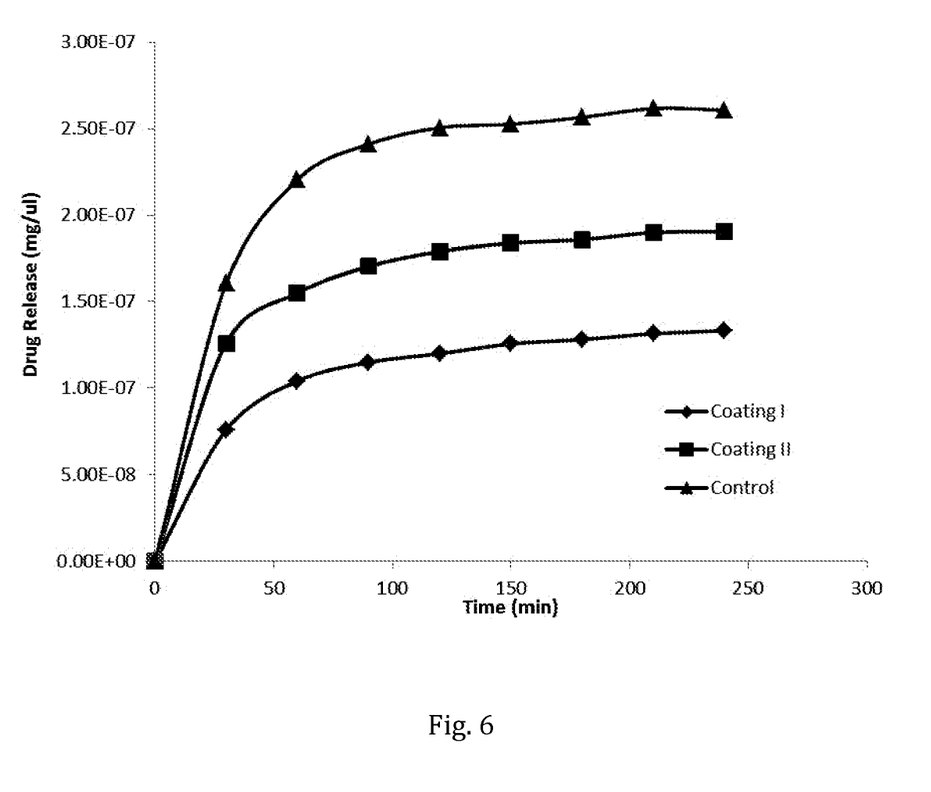
FIG. 6 shows Coating I is a medical device that consists PEG 700 diacrylate as the core (first polymeric matrix) and PEG 575 diacrylate as the second polymeric matrix. Coating II is a medical device that consists of PEG 700 diacrylate as the core (first polymeric matrix) and HEMA. TTEGDMA nanogel as the second polymeric matrix. The Control consists of PEG 700 diacrylate without any second polymeric matrix.

Two different sample devices were prepared (Coating I and Coating II as shown in FIG. 6) and tested for their ability to control release of a pharmaceutically active compound using a similar core first polymeric matrix and using a different second polymeric matrix. The pharmaceutically active compound used was dexamethasone. All samples were impregnated with dexamethasone by putting the first polymeric matrix in APS. Dexamethasone solution followed by adding a second polymeric matrix. Coating I and Coating II were able to curb the burst release that is observed from the control and thereby prolonging the sustained release of the encased Dexamethasone®.

Figure 7:
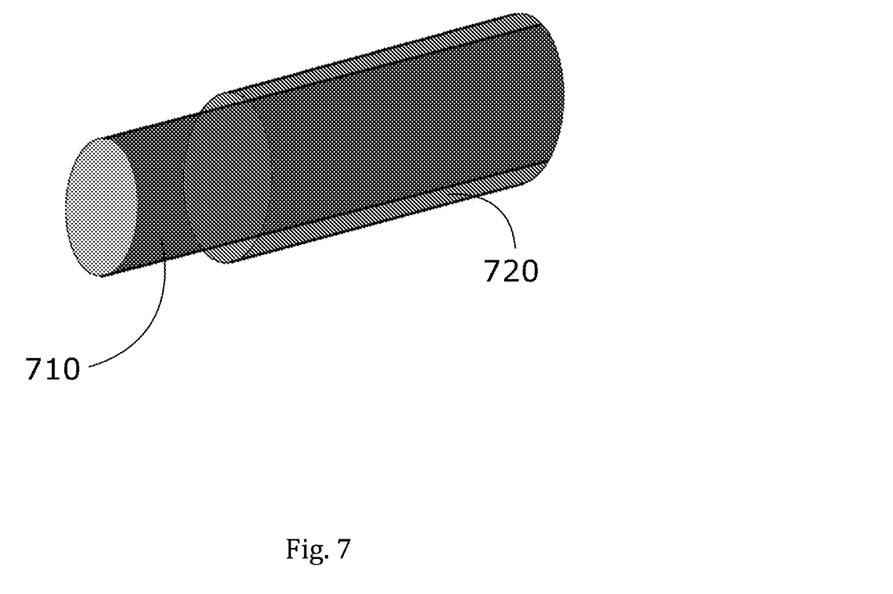
FIG. 7 shows an example of an illustrative embodiment of a medical device from the side view of a core first polymeric matrix 710 with a outer second polymeric matrix 720 that forms a clear coating of a nanogel formed at the interface of the two networks.
Figure 8:
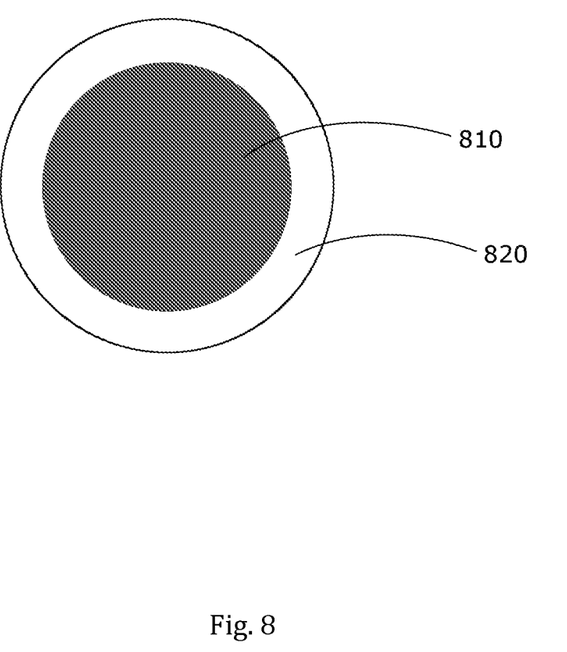
FIG. 8 shows an example of an illustrative embodiment of a medical device from a cross sectional view a core first polymeric matrix 810 (or a polymer core) with an outer second polymeric matrix 820 that forms a clear coating of a nanogel.
Figure 9:
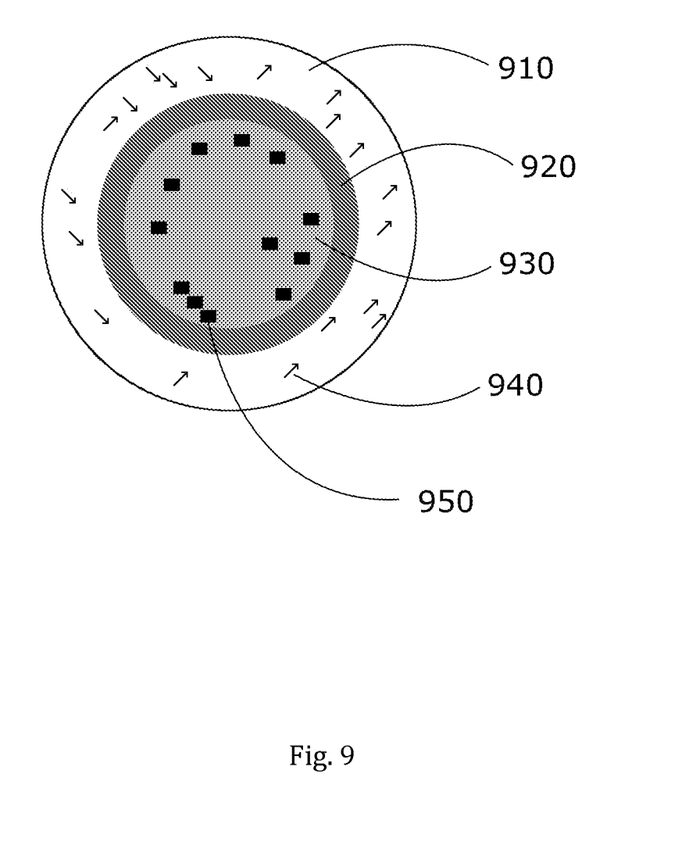
FIG. 9 shows an example of a general scheme of an illustrative embodiment of a medical device, illustrating an interfacial polymerization reaction between the first polymeric matrix 930 and the second polymeric matrix 910 that occurs at the boundary of the first polymeric matrix 930, when the first polymeric matrix 930 is immersed in a second polymeric matrix 910 (shown as a monomer solution). The polymerization is initiated when the reactive nanoscale (<50 nm) prepolymeric particles shown as reaction component 940 and reaction component 950, which form two parts of an initiating mechanism meet at the interface to initiate the reaction between unreacted functionality in the first polymeric matrix 930 and/or as monomer solution here (or second polymeric matrix 910) forming a coating (shown as coating 920 formed via interfacial polymerization).

It is understood that FIGS. 7-9 are provided by way of example only, and that other structures may be used to form embodiments of the present disclosure depending on the particular implementations.

The examples and embodiments disclosed herein provide support the fact that the burst release of the encapsulated drug can be contained and a sustained release pattern can be obtained as a result of the secondary polymeric matrix.

While the methods disclosed herein have been described and shown with reference to particular operations performed in a particular order, it will be understood that these operations may be combined, sub-divided, or re-ordered to form equivalent methods without departing from the teachings of the present disclosure. Accordingly, unless specifically indicated herein, the order and grouping of the operations is not a limitation of the present disclosure.

While the disclosure has been particularly shown and described with reference to a number of different embodiments, it would be understood by those skilled in the art that changes in the form and details may be made to the various embodiments disclosed herein without departing from the spirit and scope of the disclosure, and that the various embodiments disclosed herein are not intended to act as limitations on the scope of the claims.

What is claimed is:

1. A device comprising:
   a core that comprises a core polymeric matrix, wherein the core polymeric matrix comprises a core matrix polymer that is cross-linked, linear, or a combination thereof, wherein the core matrix polymer is selected from the group consisting of polyurethane, poly(ethylene glycol), poly(propylene glycol), polyvinyl alcohol, acrylic acid, methacrylic acid, chitosan, alginates, acrylamides, epoxies, isocyanates vinyl ethers, allyl ethers, acrylates, methacrylates, nanogels, and nanotubes;
   a nanogel layer having a thickness in a range of about 25 μm to about 140 μm, wherein the nanogel layer comprises a layer polymeric matrix, wherein the layer polymeric matrix comprises a layer matrix polymer that is cross-linked, linear, or a combination thereof, wherein the layer matrix polymer comprises hydrophilic nanogels or hydrophobic nanogels; and
   wherein the core polymeric matrix and the layer polymeric matrix are covalently linked thereby forming a polymeric macroscopic cross-linked network located at or about the interface of the core and the nanogel layer.

2. The device of claim 1 further comprising nanotubes located at or about the interface of the core and the nanogel layer.

3. The device of claim 1, wherein the core further comprises at least one pharmaceutically active compound impregnated within the core polymeric matrix and the layer polymeric matrix provides a controlled release of the at least one pharmaceutically active compound from the core.

4. The device of claim 1, wherein the core and the nanogel layer are transparent.

5. The device of claim 1, wherein the device is a contact lens or intraocular lens.

6. The device of claim 1, wherein the core polymeric matrix or the layer polymeric matrix is hydrophobic and the other of the core polymeric matrix or the layer polymeric matrix is hydrophilic.

7. The device of claim 1, wherein the core polymeric matrix or the layer polymeric matrix is selected to degrade by hydration, ultraviolet light exposure, visible light exposure, or temperature change.

8. The device of claim 1, wherein the core polymeric matrix or the layer polymeric matrix is selected to degrade by hydration, ultraviolet light exposure, visible light exposure, or temperature change; wherein the degradation occurs without any change in the shape or form of the device.

9. A method of manufacturing a device comprising:
   forming a core that comprises a core polymeric matrix, wherein the core polymeric matrix comprises a core matrix polymer that is cross-linked, linear, or a combination thereof, wherein the core matrix polymer is selected from the group consisting of polyurethane, poly(ethylene glycol), poly(propylene glycol), polyvinyl alcohol, acrylic acid, methacrylic acid, chitosan, alginates, acrylamides, epoxies, isocyanates vinyl ethers, allyl ethers, acrylates, methacrylates, nanogels, and nanotubes;
   forming a nanogel layer having a thickness in a range of about 25 μm to about 140 μm, wherein the nanogel layer comprises a layer polymeric matrix, wherein the layer polymeric matrix comprises a layer matrix polymer that is cross-linked, linear, or a combination thereof, wherein the layer matrix polymer comprises hydrophilic nanogels or hydrophobic nanogels; and covalently linking the core polymeric matrix and the layer polymeric matrix, thereby forming a device comprising the core, the nanogel layer, and a polymeric macroscopic cross-linked network located at or about the interface of the core and the nanogel layer.

10. The method of manufacturing of claim 9, further comprising:

inhibiting the polymeric macroscopic cross-linked network formed in the mold from shrinking via a covalent bond, hydrophobic interaction, hydrophilic interaction, van der Waals interaction or hydrogen bond.

11. The method of claim 9, further comprising: impregnating at least one pharmaceutically active compound within the core polymeric matrix.

12. The method of claim 9, wherein the core polymeric matrix or the layer polymeric matrix is hydrophobic and the other of the core polymeric matrix or the layer polymeric matrix is hydrophilic.

13. The method of claim 9, wherein nanotubes are formed at or about the interface of the core and the nanogel layer.

14. The method of claim 9, wherein the core and the nanogel layer are transparent.

15. The method of claim 9, wherein the device is a contact lens or intraocular lens.

16. A method of manufacturing a device comprising:

forming a mold comprising a nanogel layer, wherein the nanogel layer has a thickness in a range of about 25 µm to about 140 µm, wherein the nanogel layer comprises a layer polymeric matrix, wherein the layer polymeric matrix comprises a layer matrix polymer that is cross-linked, linear, or a combination thereof, wherein the layer matrix polymer comprises hydrophilic nanogels or hydrophobic nanogels;

forming a core that comprises a core polymeric matrix, wherein the core polymeric matrix comprises a core matrix polymer that is cross-linked, linear, or a combination thereof, wherein the core matrix polymer is selected from the group consisting of polyurethane, poly(ethylene glycol), poly(propylene glycol), polyvinyl alcohol, acrylic acid, methacrylic acid, chitosan, alginates, acrylamides, epoxies, isocyanates vinyl ethers, allyl ethers, acrylates, methacrylates, nanogels, and nanotubes;

adding the core to the mold; and covalently linking the core polymeric matrix and the layer polymeric matrix thereby forming a device comprising the mold, the core, and a polymeric macroscopic cross-linked network located at or about the interface of the mold and the core.

17. The method of claim 16, further comprising:

inhibiting the polymeric macroscopic cross-linked network in the mold from shrinking via a covalent bond, hydrophobic interaction, hydrophilic interaction, van der Waals interaction or hydrogen bond.

18. The method of claim 16, further comprising: impregnating at least one pharmaceutically active compound within the core polymeric matrix.

19. The method of claim 16, wherein the core polymeric matrix or the layer polymeric matrix is hydrophobic and the other of the core polymeric matrix or the layer polymeric matrix is hydrophilic.

20. The method of claim 16, wherein the core and the nanogel layer are transparent.

21. The method of claim 16, wherein the device is a contact lens or intraocular lens.

* * * * *